United States Patent
Yin et al.

(10) Patent No.: US 8,952,199 B2
(45) Date of Patent: Feb. 10, 2015

(54) METHODS OF AND FORMULATIONS FOR REDUCING AND INHIBITING THE GROWTH OF THE CONCENTRATION OF MICROBES IN WATER-BASED FLUIDS AND SYSTEMS USED WITH THEM

(75) Inventors: Bei Yin, Buffalo Grove, IL (US); Jingjun Yang, Round Lake, IL (US)

(73) Assignee: Dow Global Technologies LLC, Midland, MI (US)

( * ) Notice: Subject to any disclaimer, the term of this patent is extended or adjusted under 35 U.S.C. 154(b) by 984 days.

(21) Appl. No.: 12/669,657

(22) PCT Filed: Jul. 21, 2008

(86) PCT No.: PCT/US2008/070652
§ 371 (c)(1),
(2), (4) Date: Jul. 20, 2010

(87) PCT Pub. No.: WO2009/015089
PCT Pub. Date: Jan. 29, 2009

(65) Prior Publication Data
US 2010/0298275 A1  Nov. 25, 2010

Related U.S. Application Data

(60) Provisional application No. 60/951,616, filed on Jul. 24, 2007.

(51) Int. Cl.
| | | |
|---|---|---|
| C07F 9/02 | (2006.01) | |
| C10M 173/00 | (2006.01) | |
| A01N 35/02 | (2006.01) | |
| C02F 1/50 | (2006.01) | |
| C09D 5/14 | (2006.01) | |
| C10M 141/10 | (2006.01) | |

(52) U.S. Cl.
CPC ............. *C10M 173/00* (2013.01); *A01N 35/02* (2013.01); *C02F 1/50* (2013.01); *C09D 5/14* (2013.01); *C10M 141/10* (2013.01); *C10M 2207/08* (2013.01); *C10M 2215/16* (2013.01); *C10M 2215/202* (2013.01); *C10M 2215/22* (2013.01); *C10M 2219/104* (2013.01); *C10M 2223/06* (2013.01); *C10N 2230/16* (2013.01); *C10N 2240/40* (2013.01)
USPC .......................................................... 568/11

(58) Field of Classification Search
USPC ........................................................... 568/11
See application file for complete search history.

(56) References Cited

U.S. PATENT DOCUMENTS

| | | |
|---|---|---|
| 5,385,896 A | 1/1995 | Bryan et al. |
| 5,670,055 A | 9/1997 | Yu et al. |
| 5,741,757 A | 4/1998 | Cooper et al. |
| 6,784,168 B1 | 8/2004 | Jones et al. |
| 2001/0034366 A1 | 10/2001 | Beilfuss et al. |
| 2003/0092584 A1 | 5/2003 | Crews |
| 2003/0228373 A1 | 12/2003 | Ludensky et al. |
| 2004/0082473 A1 | 4/2004 | Beilfuss et al. |
| 2004/0087448 A1 | 5/2004 | Smith et al. |
| 2004/0102501 A1 | 5/2004 | Lutz et al. |
| 2008/0004189 A1 | 1/2008 | Smith et al. |

FOREIGN PATENT DOCUMENTS

| | | | |
|---|---|---|---|
| EP | 0209260 | 1/1987 | |
| EP | 0385801 A1 * | 5/1990 | ............. A01N 57/34 |
| EP | 0 385 801 A1 | 9/1990 | |
| EP | 1 402 778 A1 | 3/2004 | |
| JP | 2273605 | 11/1990 | |
| JP | 3041009 A | 2/1991 | |
| JP | 11071213 A | 3/1999 | |
| JP | 11222408 | 8/1999 | |
| JP | 11222408 A | 8/1999 | |
| JP | 2000-290112 A | 10/2000 | |
| JP | 2001526679 | 12/2001 | |
| JP | 2004115516 | 4/2004 | |
| JP | 2006527652 | 12/2006 | |
| WO | WO9613502 | 5/1996 | |
| WO | 03/062149 A2 | 7/2003 | |
| WO | 2004/017736 A1 | 3/2004 | |
| WO | WO2004113236 | 12/2004 | |

(Continued)

OTHER PUBLICATIONS

Database WPI Week 199943 Thomson Scientific, London, GB; AN 1999-512415 XP002546000 & JP 11 222408 A (Katakura Kagaku Kogyo Kenkyusho KK) Aug. 17, 1999.

(Continued)

*Primary Examiner* — Paul Zarek
(74) *Attorney, Agent, or Firm* — Tifani M. Edwards

(57) ABSTRACT

The present invention provides methods and formulations for reducing or inhibiting increase in the concentration of microbes in a water-based fluid. The methods and formulations of the present invention use glutaraldehyde and a hydroxymethyl-substituted phosphorus compound selected from the group consisting of tetrakis(hydroxymethyl)phosphonium salts, $C_1$-$C_3$ alkyl- and alkenyltris(hydroxymethyl) phosphonium salts and tris(hydroxymethyl)phosphine, in a ratio of hydroxymethyl-substituted phosphorus compound to glutaraldehyde in the range of about 2:1 to about 7:1, or about 3.5:1 to about 7.5:1. The methods and formulations of the present invention can be useful in treating water contaminated with aerobic or anaerobic bacteria in oilfield and other industrial applications.

14 Claims, No Drawings

(56) References Cited

FOREIGN PATENT DOCUMENTS

| WO | 2005/074688 A2 | 8/2005 |
|---|---|---|
| WO | WO2009/015088 | 1/2009 |

OTHER PUBLICATIONS

"Bioban CS-1135" [Online] (Oct. 10, 2002), Dow, XP002545999 Retrieved from the Internet: URL:http://www.dow.com/biocides/prod/bbcs1135.htm> [retrieved on Sep. 16, 2009].
"Bioban CS-1246" [0nline] (Oct. 10, 2002), Dow, XP002513771 Retrieved from the Internet: URL:http://www.dow.com/biocides/prod/bbcs1246.htm> [retrieved on Sep. 16, 2009].
Database WPI Week 199921 Thomson Scientific, London, GB; AN 1999-248392 XP002546071 & JP 11 071213 A (Katakura Kagaku Kogyo Kenkyusho KK) Mar. 16, 1999.
PCT International Search Report and Written Opinion, PCT International Application No. PCT/US/2008/070651, mailed Oct. 5, 2009.
PCT International Search Report and Written Opinion, PCT International Application No. PCT/US/2008/070652, mailed Oct. 6, 2009.
U.S. Appl. No. 12/669,667, Methods of and Formulations for Reducing and Inhibiting the Growth of the Concentration of Microbes in Water-Based Fluids and Systems Used with Them, filed Jan. 19, 2010.
U.S. Appl. No. 12/669,667, Office Action mailed Jul. 19, 2012.
Notice of Reasons for Rejection, Japanese Patent Application No. 2010-518320, mailed Jan. 22, 2013.
U.S. Appl. No. 12/669,667, Office Action mailed Jan. 23, 2013.

* cited by examiner

METHODS OF AND FORMULATIONS FOR REDUCING AND INHIBITING THE GROWTH OF THE CONCENTRATION OF MICROBES IN WATER-BASED FLUIDS AND SYSTEMS USED WITH THEM

CROSS-REFERENCE TO RELATED APPLICATIONS

This application is a US National Phase of International Application No. PCT/US2008/070652, filed on Jul. 21, 2008, which claims the benefit of priority to U.S. Provisional Application No. 60/951,616, filed on Jul. 24, 2007, all of which are incorporated by reference in their entirety herein.

BACKGROUND OF THE INVENTION

1. Field of the Invention

The present invention relates generally to biocides. The present invention relates more particularly to biocidal mixtures of glutaraldehyde and hydroxymethyl-substituted phosphorus compounds, and methods of using them.

2. Technical Background

Protecting water-based fluids (e.g., in injection and production systems) from microbial contamination is vital for the efficiency and success of any oil or natural gas production operation. Metabolic activity of microorganisms can cause microbiologically influenced corrosion (MIC) on metal surfaces of equipment and cause degradation of polymer additives. Biofilms formed by both aerobic and anaerobic bacteria can physically plug oil and gas pipelines and water purification systems, as well as reduce efficiency of pumps and heat transfer systems. Moreover, certain anaerobic bacteria, known as sulfate reducing bacteria, can reduce sulfate to produce hydrogen sulfide, which can sour oil and gas, corrode pipelines and storage tanks and cause deposits of iron sulfide. Microbial contamination can occur anywhere throughout the oil and natural gas field during oil and gas production operations. For example, although aerobic and anaerobic bacteria coexist in many environments, aerobic bacteria are more often found topside (i.e., near the surface) in injection water, produced water, and functional water-based fluids such as drilling muds, completion or workover fluids, stimulation fluids, fracturing fluids, and hydrotest fluids. Anaerobic bacteria, on the other hand, are most commonly found downhole (i.e., underground) in oil or gas reservoirs, near bore areas, in produced fluids, in deaeration towers, in transmission pipelines, and in the water bottoms of oil and gas storage tanks.

Biological contamination is a major complication in many other industrial processes and systems. Pulp and paper water, cooling water (e.g., in cooling towers), boiler water, industrial process water, ballast water, wastewater, metalworking fluids, water purification and treatment systems, water-based slurry, ink and tape joint compounds, water-based household products and personal care products, latex, paint, coatings and components thereof are all vulnerable to contamination by aerobic and anaerobic bacteria.

SUMMARY OF THE INVENTION

Biocides are commonly used to control the growth of microorganisms in aqueous systems. However, many are not entirely effective at controlling all types of bacterial growth and some are incompatible with other water treatment additives. The inventors have determined that there remains a need for biocidal treatment methods and formulations having increased efficiency over current systems.

One aspect of the invention is a method of reducing or inhibiting increase in the concentration of microbes in a water-based fluid or in a system used with a water-based fluid, the method comprising contacting the water-based fluid or system with glutaraldehyde and a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine, wherein the ratio of the hydroxymethyl-substituted phosphorus compound to glutaraldehyde is in the range of about 3.5:1 to about 7.5:1.

Another aspect of the invention is a formulation for reducing or inhibiting increase in the concentration of microbes in a water-based fluid or in a system used with a water-based fluid, the formulation comprising glutaraldehyde and a hydroxymethyl-substituted phosphorus compound selected from the group consisting of tetrakis(hydroxymethyl)phosphonium salts, $C_1$-$C_3$ alkyl- and alkenyltris(hydroxymethyl) phosphonium salts and tris(hydroxymethyl)phosphine, wherein the ratio of the hydroxymethyl-substituted phosphorus compound to glutaraldehyde is in the range of about 3.5:1 to about 7.5:1.

Another aspect of the invention is a method of reducing or inhibiting increase in the concentration of anaerobic microbes in a water-based fluid in an anaerobic environment or in an anaerobic part of a system used with a water-based fluid, the method comprising: contacting the water-based fluid with glutaraldehyde and a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine, wherein the ratio of hydroxymethyl-substituted phosphorus compound to glutaraldehyde is in the range of about 2:1 to about 7:1.

The present invention is capable of providing a number of advantages over the prior art. For example, use of glutaraldehyde and a hydroxymethyl-substituted phosphorus compound in the recited ratios can unexpectedly maximize synergy between the two components in a wide range of applications. Moreover, different types of microbes are most efficiently controlled using different ratios of components; this unexpected result allows the skilled artisan to tailor the use of biocides to a particular environment. The methods and formulations of the present invention can be used at relatively low biocide loadings, reducing cost, odor, worker exposure and environmental effects. In certain embodiments of the invention, the biocidal treatment can be carried out in the absence of a quaternary ammonium salt, and therefore allows the unhindered use of anionic polymers for flocculation and purification. Additional features and advantages of the invention will be set forth in the detailed description which follows and will be readily apparent to those skilled in the art from the description or recognized by practicing the invention as described in the written description and claims hereof, as well as in the appended drawings.

It is to be understood that both the foregoing general description and the following detailed description are merely exemplary of the invention, and are intended to provide an overview or framework for understanding the nature and character of the invention as it is claimed.

DETAILED DESCRIPTION OF THE INVENTION

One aspect of the invention is a method of reducing or inhibiting an increase in the concentration of microbes in a water-based fluid or in a system used with a water-based fluid. The method comprises contacting the water-based fluid or system with glutaraldehyde and a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine.

Water-based fluids treatable using the methods of the present invention can be found in many forms. For example, the water-based fluid can exist as a volume of water or aqueous solution. Alternatively, the water-based fluid can be a slurry or suspension, or can be the liquid fraction of a mud, pulp, or other mixed-phase system. As the skilled artisan will appreciate, the water-based fluids treatable according to the present invention may include other substances, such as anionic polymers, demulsifiers, corrosion inhibitors, scale inhibitors and/or surfactants. Depending on the application, the water-based fluids can also include other appropriate substances, such as thickeners (e.g., clays, polymers), salts, density increasing substances (e.g., barite), lubricants and viscosity modifiers. Similarly, systems used with water-based fluids take many forms, and include, for example, systems used in water purification, oil or natural gas production and transmission, paper- and pulpmaking, metalworking, heating and cooling, storage, and cleaning and rinsing processes.

Glutaraldehyde is commonly available as a concentrated (e.g., 25 wt %, 50 wt %) solution in water. Members of the UCARCIDE™ family of glutaraldehyde antimicrobials, available from The Dow Chemical Company, are suitable for use in the present invention. Glutaraldehyde is also available neat as a colorless, slightly oily liquid.

Hydroxymethyl-substituted phosphorus compounds are also generally available both in undissolved form or as aqueous solutions. In one embodiment of the invention, the hydroxymethyl-substituted phosphorus compound is a tetrakis(hydroxymethyl)phosphonium salt. For example, the hydroxymethyl-substituted phosphorus compound can be tetrakis(hydroxymethyl)phosphonium sulfate (THPS). THPS is available from The Dow Chemical Company as AQUCAR™ THPS 75, a 75 wt % solution in water. Other tetrakis(hydroxymethyl)phosphonium salts, such as tetrakis (hydroxymethyl)phosphonium chloride, can also be used. In other embodiments of the invention, the hydroxymethyl-substituted phosphorus compound is a $C_1$-$C_3$ alkyl- and alkenyltris(hydroxymethyl)phosphonium salt or tris(hydroxymethyl)phosphine. Of course, more than one of the recited hydroxymethyl-substituted phosphorus compounds can be combined for use in the present invention; in such cases, ratios and concentrations are calculated using the total weight of all hydroxymethyl-substituted phosphorus compounds.

In some methods according to this aspect of the invention, the ratio of the hydroxymethyl-substituted phosphorus compound to glutaraldehyde is in the range of about 2:1 to about 7:1, or in the range of about 3.5:1 to about 7.5:1. As described in more detail below, the inventors have unexpectedly found that the use of hydroxymethyl-substituted phosphorus compounds and glutaraldehyde in the recited ratios can provide better biocidal activity than the use of either substance alone or in combination at different ratios. In certain embodiments of the invention, the ratio of the hydroxymethyl-substituted phosphorus compound to glutaraldehyde is in the range of about 3.7:1 to about 6.3:1. For example, the ratio of the hydroxymethyl-substituted phosphorus compound to glutaraldehyde can be in the range of about 3.7:1 to about 5:1, or in the range of about 5.7:1 to about 6.3:1. All ratios discussed herein are weight/weight, unless otherwise noted. The methods of the present invention can be used in a variety of applications to treat a wide variety of water-based fluids, such as oil field and natural gas field water and functional fluids or components of the functional fluids (e.g. drilling muds, completion and workover fluids, stimulation fluids, packing fluids, fracturing fluids, hydrotest fluids), pulp or paper water and slurry, cooling water, boiler water, industrial process water, ballast water, wastewater, metalworking fluids, hydrocarbon oil and natural gas, water-based slurry, ink and tape joint compounds, water-based household products and personal care products, latex, paint and coatings. As used herein, "water-based fluid" includes hydrocarbon oil and natural gas that may have an aqueous phase associated therewith. The methods of the present invention can be especially useful in treating oilfield and natural gas field water and functional fluids and oil and gas transmission and storage systems. The methods of the present invention can also be used in a variety of systems used with water-based fluids, such as those used in heating, cooling, oil and natural gas production, paper production. The methods of the present invention can also be used to control bacteria and prevent biofouling in water purification systems, such as those using reverse osmosis membranes, microfiltration membranes or ultrafiltration membranes, as well as those using sand filtration, multimedia filtration, active carbon filtration, ion exchange and electrodionization.

The inventors have further unexpectedly discovered that combinations of glutaraldehyde and hydroxymethyl-substituted phosphorus compound have different effects on aerobic bacteria and anaerobic sulfate reducing bacteria. In one embodiment of the invention, the microbes are aerobic bacteria. Aerobic bacteria can be most efficiently treated using ratios of hydroxymethyl-substituted phosphorus compound to glutaraldehyde in the range of about 3.5:1 to about 5.5:1. In certain embodiments of the invention, aerobic bacteria are treated using a ratio of hydroxymethyl-substituted phosphorus compound to glutaraldehyde in the range of about 3.7:1 to about 5:1. These ratios can be useful in reducing and/or maintaining microbial concentrations in water-based fluids and systems in which aerobic bacteria are dominant, such as topside or surface oilfield and natural gas field water, components of oil and gas field drilling muds, completion and workover water-based fluids, stimulation fluids, packing fluids, fracturing water-based fluids, hydrotest fluids, hydrocarbon oil and gas, water-based slurry, ink and tape joint compounds, water-based household products and personal care products, latex, paint, coatings, metalworking fluids and systems, ballast water, cooling water, boiler water, pulp or paper processing systems or water-based fluids associated therewith, industrial process water, and other open systems and water-based fluids therein.

Moreover, glutaraldehyde and hydroxymethyl-substituted phosphorus compounds have different but complementary trends of activity against aerobic and anaerobic bacteria with respect to treatment time. Glutaraldehyde has higher efficacy against aerobic bacteria than do hydroxymethyl-substituted phosphorus compounds. Hydroxymethyl-substituted compounds exhibit higher ultimate efficacy for anaerobic sulfate reducing bacteria than does glutaraldehyde, but glutaraldehyde does provide more rapid results.

According to another embodiment of the invention, the microbes are anaerobic bacteria. For example, the microbes can be anaerobic sulfate reducing bacteria. Anaerobic bacteria (e.g., anaerobic sulfate reducing bacteria) can be most efficiently treated using ratios of hydroxymethyl-substituted phosphorus compound to glutaraldehyde in the range of about 2:1 to about 7:1. For example, anaerobic bacteria can be treated using ratios of hydroxymethyl-substituted phosphorus compound to glutaraldehyde in the range of about 4:1 to about 7:1. In certain embodiments of the invention, anaerobic bacteria are treated using a ratio of hydroxymethyl-substituted phosphorus compound to glutaraldehyde in the range of about 5:1 to about 6.5:1. For example, anaerobic bacteria can be treated using a ratio of hydroxymethyl-substituted phosphorus compound to glutaraldehyde in the range of about 5.7:1 to about 6.3:1. These ratios can be useful in reducing and/or maintaining microbial concentrations in water-based fluids and systems in which anaerobic bacteria are dominant, such as injection water and fluids in oil and natural gas reservoirs, produced water and fluids in oil and gas production operations, oil or gas storage tanks or water-based fluids therein, deaeration towers or water-based fluids therein, transmission pipelines or water based fluids therein, wastewater treatment systems and water-based fluids therein, and closed systems and lower parts of open systems and water-based fluids therein.

The skilled artisan can select final working concentrations of glutaraldehyde and the hydroxymethyl-substituted phosphorus compound necessary to provide the desired antimicrobial effect. For example, according to one embodiment of the invention, the combined concentration of glutaraldehyde and hydroxymethyl-substituted phosphorus compound in the water-based fluid or system is in the range of about 5 ppm to about 1500 ppm. The combined concentration of glutaraldehyde and hydroxymethyl-substituted phosphorus compound in the water-based fluid or system can be in the range of about 10 ppm to about 500 ppm. In certain embodiments of the invention, the combined concentration of glutaraldehyde and hydroxymethyl-substituted phosphorus compound in the water-based fluid or system is in the range of about 50 ppm to about 200 ppm, or in the range of about 10 ppm to about 100 ppm. In other embodiments of the invention, the combined concentration of oxazolidine compound and hydroxymethyl-substituted phosphorus compound in the water-based fluid or system can be in the range of about 1 ppm to about 20000 ppm.

According to one embodiment of the invention, during the contacting step the water-based fluid or system is free of or substantially free of quaternary ammonium compounds. For example, the water-based fluid or system can have less than 100 ppm, less than 25 ppm, less than 5 ppm, or even less than 1 ppm. The inventors have found ratios of hydroxymethyl-substituted phosphorus compound and glutaraldehyde that provide biocidal efficiency without the use of quaternary ammonium compounds. In this embodiment of the invention, therefore, the water-based fluid can contain at least one anionic polymer, demulsifier, corrosion inhibitor, scale inhibitor and/or surfactant without suffering a reduction in efficacy due to the presence of (e.g., through precipitation by) quaternary ammonium species.

In certain embodiments of the invention, during the contacting step the water-based fluid or system is free of or substantially free of adducts between formaldehyde and $C_2$-$C_6$ aliphatic glycol or $C_2$-$C_6$ aliphatic glycol mono $C_1$-$C_4$ alkyl ether. For example, the water based fluid can have a concentration of adducts between formaldehyde and $C_2$-$C_6$ aliphatic glycol or $C_2$-$C_6$ aliphatic glycol mono $C_1$-$C_4$ alkyl ether of less than about 100 ppm, less than 25 ppm, less than 5 ppm, or even less than 1 ppm.

In certain embodiments of the invention, the method includes contacting the water-based fluid or system with at least one additional biocide. The skilled artisan will choose the identity and concentration of the additional biocide based on the particular application envisioned. Suitable additional biocides include, for example, 2,2-dibromo-2-nitrilopropionamide (DBNPA), 2-bromo-2-nitropropane-1,3-diol (bronopol), 2-methyl-4-isothiazolin-3-one (MIT), tris(hydroxymethyl)nitromethane, 1-(3-chloroallyl)-3,5,7-triaza-1-azonia-adamantane chloride, 1,2-benzisothiazolin-3-one, and o-phthalaldehyde.

In some embodiments of the invention, the water-based fluid or system is contacted with glutaraldehyde and the hydroxymethyl-substituted phosphorus compound at more than one ratio of hydroxymethyl-substituted phosphorus compound to glutaraldehyde. For example, in one embodiment of the invention, the water-based fluid is contacted at a first ratio of hydroxymethyl-substituted phosphorus compound to glutaraldehyde in the range of about 3.5:1 to about 7.5:1; and also contacted at a second ratio of hydroxymethyl-substituted phosphorus compound to glutaraldehyde in the range of about 2:1 to about 7:1, in which the first ratio is different than the second ratio. For example, the first ratio can be in the range of about 3.5:1 to about 5:1, or in the range of about 3.7:1 to about 4:1, and the second ratio can be in the range of about 2:1 to about 7:1, in the range of about 4:1 to about 7:1, or in the range of about 5:1 to about 6.5:1. The contacting at the first ratio can be performed before the contacting at the second ratio. Alternatively, the contacting at the second ratio can be performed before the contacting at the first ratio. The methods according to these embodiments of the invention can be used to reduce or prevent microbial contamination in a water-based fluid or system over time. As the skilled artisan will appreciate, as a water-based fluid moves through a system or process, or as the process taking place in a system evolves, it can be subject to contamination by different types of microbes. At a position or time where the water-based fluid or system is at risk of contamination by aerobic microbes, it can be contacted at a ratio in the range of about 3.5:1 to about 5:1. Similarly, at a position or time in a system or process where the water-based fluid is at risk of contamination by anaerobic microbes, it can be contacted at a ratio in the range of about 2:1 to about 7:1 (e.g., in the range of about 4:1 to 7:1). For example, water or a functional fluid is often injected downhole into an oil or natural gas well to enhance the productivity of the oil or gas well. The water or functional fluid can initially be contacted at a ratio in the range of about 3.5:1 to about 5:1 in order to achieve better control of aerobic microbes. At a later point, for example when the water enters a deaeration tower and/or immediately before the water or functional fluid is injected downhole, it can be contacted at a ratio in the range of about 2:1 to about 7:1 (e.g., in the range of about 4:1 to about 7:1) to obtain and maintain better control of anaerobic microbes in deaeration towers and/or downhole areas. In souring wells, produced fluids can first be treated at higher ratios of hydroxymethyl-substituted phosphorus compound to glutaraldehyde in order to reduce anaerobic sulfate-reducing bacteria and hydrogen sulfide. After oil/gas/water separation, the produced water can be treated with a lower ratio of hydroxymethyl-substituted phosphorus compound to glutaraldehyde before release or reinjection in order to better control aerobic microbes.

The contacting can be performed in many different ways, depending on factors such as the type of water-based fluid or system being treated and its location in an oil or natural gas production or other industrial system or process. For example, the glutaraldehyde and the hydroxymethyl-substituted phosphorus compound can be added to the water-based fluid or system at substantially the same time. For example, the glutaraldehyde and the hydroxymethyl-substituted phosphorus compound can be provided as a mixture in the desired ratio, which is added to the water-based fluid or system. Alternatively, the glutaraldehyde can be added to the water-based fluid or system at substantially the same time as the hydroxymethyl-substituted phosphorus compound by adding one after the other with little delay (i.e., 3 minutes or less) between additions. In other embodiments of the invention, the glutaraldehyde and the hydroxymethyl-substituted phosphorus compound are added to the water-based fluid or system at different times (i.e., with a delay of more than 3 minutes). In these embodiments of the invention, the glutaraldehyde and hydroxymethyl-substituted phosphorus compound components are added to yield after addition the desired final concentration and ratio in the water-based fluid or system. The glutaraldehyde and hydroxymethyl-substituted phosphorus compound may be added in a single dose (or "slug") to a pipeline, reservoir or other part of a system, or may be added together in multiple slugs. The glutaraldehyde and hydroxymethyl-substituted phosphorus compound may alternatively be continuously added to the water-based fluid or system in order to maintain a desired concentration and ratio of components. When the method is used with a system, system components can be contacted with glutaraldehyde and the hydroxymethyl-substituted phosphorus compound in an assembled and/or operational state. System components can also be contacted with glutaraldehyde and the hydroxymethyl-substituted phosphorus compound in a separate bath or fluid circulation system. For example, in methods of the invention used to treat a water purification system, glutaraldehyde and the hydroxymethyl-substituted phosphorus compound can be pumped through the entire system (e.g., by adding them to the feed water while the system is on-line). A single system component (e.g., a membrane) can also be isolated or removed and separately treated with glutaraldehyde and the hydroxymethyl-substituted phosphorus compound off-line in a feed tanker.

Another aspect of the invention is a method of reducing or inhibiting an increase in the concentration of anaerobic microbes in a water-based fluid in an anaerobic environment or in an anaerobic part of a system used with a water-based fluid. The method comprises contacting the water-based fluid with glutaraldehyde and a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine. As described above, the ratio of hydroxymethyl-substituted phosphorus compound is in the range of about 2:1 to about 7:1, in the range of about 4:1 to about 7:1, or in the range of about 5:1 to about 6.5:1. As described in more detail below, such ratios unexpectedly provide synergistic reduction of anaerobic bacteria (especially anaerobic sulfate reducing bacteria). In one embodiment of the invention, the anaerobic environment is within an oil or natural gas field. The methods according to this aspect of the invention can be adapted and varied as described above.

Another aspect of the invention is a formulation for reducing or inhibiting increase in the concentration of microbes in a water-based fluid or in a system used with a water-based fluid. The formulation includes glutaraldehyde and a hydroxymethyl-substituted phosphorus compound selected from the group consisting of tetrakis(hydroxymethyl)phosphonium salts, $C_1$-$C_3$ alkyl- and alkenyltris(hydroxymethyl) phosphonium salts and tris(hydroxymethyl)phosphine. The ratio of hydroxymethyl-substituted phosphorus compound to glutaraldehyde is in the range of about 3.5:1 to about 7.5:1. For example, as described above with respect to the methods of the present invention, the ratio of hydroxymethyl-substituted phosphorus compound to glutaraldehyde can be in the range of about 3.7:1 to about 6.3:1; in the range of about 3.5:1 to about 5.5:1; in the range of about 3.7:1 to about 5:1; in the range of about 4:1 to about 7:1; in the range of about 5:1 to about 6.5:1; or in the range of about 5.1:1 to about 6.3:1.

The formulation can have a wide variety of overall concentrations of glutaraldehyde and hydroxymethyl-substituted phosphorus compound. In certain embodiments of the invention, the total concentration of glutaraldehyde and hydroxymethyl-substituted phosphorus compound in the formulation is in the range of about 0.1 wt % to about 99 wt %. For example, the total concentration of glutaraldehyde and hydroxymethyl-substituted phosphorus compound in the formulation can be in the range of about 5 wt % to about 80 wt %, or in the range of about 15 wt % to about 50 wt %. During dosing of the aqueous system being treated, the user can dilute concentrated formulations to more appropriate end-use concentrations for a particular application (e.g., in the range of about 1 to about 1500 ppm; 5 ppm to about 500 ppm; in the range of about 10 ppm to about 350 ppm; in the range of about 50 ppm to about 200 ppm; or in the range of about 10 ppm to about 100 ppm).

In certain embodiments of the invention, the formulation also includes water. For example, the water concentration of the formulation can be in the range of about 1 wt % to about 99 wt %; in the range of about 20 wt % to about 95 wt %; or in the range of about 50 wt % to about 85 wt %. Of course, other solvents, such as lower alcohols, glycols, glycol ethers and esters and dimethylformamide, can be used in the formulations of the present invention in addition to or in place of water.

The formulations of the present invention can be prepared using methods standard in the formulation arts. For example, it will often be convenient to simply blend commercially-available concentrated aqueous solutions (such as UCARCIDE™ solutions for glutaraldehyde and AQUCAR™ THPS 75 for THPS) in proportions appropriate to yield the desired ratios. Other additives can be added as desired, and water (and/or other solvents) can be added to further dilute the formulation to a desired total concentration.

In one embodiment of the invention, the hydroxymethyl-substituted phosphorus compound is a tetrakis(hydroxymethyl)phosphonium salt. For example, the hydroxymethyl-substituted phosphorus compound can be tetrakis(hydroxymethyl)phosphonium sulfate. Of course, other tetrakis(hydroxymethyl)phosphonium salts, such as tetrakis(hydroxymethyl)phosphonium chloride, can also be used.

In certain embodiments of the invention, the formulation is free or substantially free of quaternary ammonium compounds. For example, the formulation can have less than 10 wt %, less than 1 wt %, or even less than 0.25 wt % quaternary ammonium compounds. As described above, quaternary ammonium compounds can be disfavored when additives such as anionic polymers, demulsifiers, corrosion inhibitors and/or surfactants are to be used. Accordingly, in this embodiment of the invention, the formulation can include at least one anionic polymer, demulsifier, corrosion inhibitor, scale inhibitor and/or surfactant. Of course, in other embodiments of the invention, the formulation can include a quaternary ammonium compound.

In certain embodiments of the invention, the formulation is free or substantially free of adducts between formaldehyde and $C_2$-$C_6$ aliphatic glycol or $C_2$-$C_6$ aliphatic glycol (mono $C_1$-$C_4$ alkyl ether). For example, the formulation can have less than 10 wt %, less than 1 wt %, or even less than 0.25 wt % adducts between formaldehyde and $C_2$-$C_6$ aliphatic glycol or $C_2$-$C_6$ aliphatic glycol (mono $C_1$-$C_4$ alkyl ether).

In certain embodiments of the invention, the formulation includes at least one additional biocide. The skilled artisan can select the identity and concentration of the additional biocide based on the particular application envisioned. Suitable additional biocides include, for example, 2,2-dibromo- 2-nitrilopropionamide (DBNPA), 2-bromo-2-nitropropane-1,3-diol (bronopol), 2-methyl-4-isothiazolin-3-one (MIT), tris(hydroxymethyl)nitromethane, 1-(3-chloroallyl)-3,5,7-triaza-1-azonia-adamantane chloride, 1,2-benzisothiazolin-3-one, and o-phthalaldehyde.

The formulations of the present invention can include other substances, depending on the ultimate application. However, in one embodiment of the invention the formulations consist essentially of glutaraldehyde, the hydroxymethyl-substituted phosphorus compound, and water.

Other aspects of the invention include embodiments that combine not inconsistent aspects from one or more of the embodiments described above. For example, one embodiment described above uses THPS as the hydroxymethyl-substituted phosphorus compound, and another embodiment described above the system being treated is free of quaternary ammonium compounds. Accordingly, in yet another embodiment of the invention, the hydroxymethyl-substituted phosphorus compound is THPS and the system being treated is free of quaternary ammonium compounds.

The methods and formulations of the present invention can be adapted for use in many applications. For example, the methods and formulations of the present invention can be used in many phases of oil or natural gas production, transmission, and storage, both topside and downhole, such as in aeration towers, storage tanks, injection water, production water, pigging operations, drilling muds, completion or workover fluids, stimulation fluids, packing fluids, fracturing fluids and hydrotest fluids. The methods and formulations can be used in water treatment and purification processes and systems, for example to treat membranes and other system components that are susceptible to fouling. The methods and formulations can also be used in paper and pulp production, ballast water disinfection and in other industrial processes. The methods and formulations can help prevent microbial contamination of water-based fluids and systems used in cooling and heating processes. The methods and formulations can also be used to prevent microbial contamination of water-based slurry, ink and tape-joint compounds, water-based household products and personal care products, latex, paint and coatings. Of course, the methods and formulations of the present invention can also be used in other processes and apparati not mentioned specifically herein.

EXAMPLES

Comparative Example 1

Efficacy of Glutaraldehyde and THPS Individually Against Aerobic Bacteria vs. Time A sterile salt solution (1.2490 g NaCl, 2.9290 g NaHCO$_3$, 0.1910 g Na$_2$CO$_3$, 0.0060 g Na$_2$SO$_4$, 0.033 g CaCl$_2$, and 0.0590 g MgCl$_2$.6H2O in 1 L water) is contaminated with mixed oil/gas field aerobic bacteria at final bacterial concentrations of ~10$^7$ CFU/mL. At day zero, either glutaraldehyde (UCARCIDE™ 250, 50% glutaraldehyde in water, The Dow Chemical Company) or THPS (AQUCAR™ THPS 75, 75% THPS in water, The Dow Chemical Company) is added and the solution mixed well to provide a desired final concentration. The solution is then incubated at 37° C. Bacterial populations are monitored over time using a serial dilution method. In experiments running over seven days, samples are reinoculated at day seven.

Table 1 shows the biocide concentration necessary to achieve at least 3 Log (i.e., 99.9%) reduction of bacteria at various times.

| Time Interval | Concentration required for glutaraldehyde to achieve at least 3 log reduction of aerobic bacteria (ppm, active) | Concentration required for THPS to achieve at least 3 log reduction of aerobic bacteria (ppm, active) |
|---|---|---|
| 2 hrs | 25.0 | 25.0 |
| 4 hrs | 25.0 | 25.0 |
| 1 day | 6.3 | 12.5 |
| 3 days | 6.3 | 12.5 |
| 4 days | 6.3 | 25.0 |
| 7 days | 12.5 | 25.0 |
| 8 days | 25.0 | 100.0 |
| 9 days | 25.0 | 100.0 |

Comparative Example 2

Efficacy of Glutaraldehyde and THPS Individually Against Anaerobic Sulfate-Reducing Bacteria vs. Time A sterile salt solution as described in Example 1 is deaerated, then contaminated with mixed oil/gas field anaerobic sulfate reducing bacteria at final bacterial concentrations of ~10$^7$ CFU/mL. At time=zero, either glutaraldehyde (UCARCIDE™ 250) or THPS (AQUCAR™ THPS 75) is added and the solution mixed well to provide a desired final concentration. The solutions are incubated at 37° C. in an anaerobic environment (Bactron III anaerobic chamber). Bacterial populations are monitored over time using a serial dilution method. In experiments running over seven days, samples are reinoculated at day seven.

Table 2 shows the biocide concentration necessary to achieve at least at least 3 Log (i.e., 99.9%) reduction of bacteria at various times.

| Time Interval | Concentration required for glutaraldehyde to achieve at least 3 log reduction of anaerobic sulfate reducing bacteria (ppm, active) | Concentration required for THPS to achieve at least 3 log reduction of anaerobic sulfate reducing bacteria (ppm, active) |
|---|---|---|
| 2 hrs | 12.5 | 50.0 |
| 4 hrs | 12.5 | 25.0 |
| 1 day | 12.5 | 25.0 |
| 2 days | 12.5 | 12.5 |
| 3 days | 25.0 | 6.3 |
| 4 days | 25.0 | 6.3 |
| 7 days | 25.0 | 6.3 |
| 8 days | 25.0 | 12.5 |
| 9 days | 50.0 | 25.0 |

Example 3

Synergistic Activity of Glutaraldehyde and THPS Against Various Bacteria

The synergy between glutaraldehyde and THPS is measured by determining the "synergy index" for various ratios of THPS:glutaraldehyde. The synergy index is calculated as Synergy Index=$(Ca/CA)+(Cb/CB)$, in which Ca is the concentration of THPS required to achieve 3 log or more bacterial reduction when used in combination with glutaraldehyde at the specified ratio;

CA is the concentration of THPS required to achieve 3 log or more bacterial reduction when used alone;

Cb is the concentration of glutaraldehyde required to achieve 3 log or more bacterial reduction when used in combination THPS with at the specified ratio; and CB is the concentration of glutaraldehyde required to achieve 3 log or more bacterial reduction when used alone.

When the synergy index is less than 1, the compounds work together synergistically. When the synergy index is 1, the compounds have strictly additive effect. When the synergy index is greater than 1, the compounds are antagonistic to one another.

The testing protocols described in Examples 1 and 2, respectively, are used for oil/gas field aerobic bacteria and anaerobic sulfate reducing bacteria. For the standard bacterial strains *Enterobacter aerogenes* ATCC 13048, *Salmonella choleraesius* ATCC 10708, *Pseudomonas aeruginosa* ATCC 10145, *Staphylococcus aureus* ATCC 6538, *Klebsiella pneumoniae* ATCC 8308, *Bacillus subtillus* ATCC 8473, *Escherichia coli* ATCC 11229, and *Pseudomonas aeruginosa* ATCC 39451, separate experiments are performed as described in Example 1, but using a sterile 0.85% NaCl solution instead of the salt solution. For standard marine bacteria *Pseudomonas* sp. ATCC 39451, experiments are performed as described in Examples 1 and 2, but at pH 8.0 using artificial sea water (24.6 g NaCl, 0.67 g KCl, 1.36 g $CaCl_2.2H_2O$, 6.29 g $MgSO_4.7H_2O$, 4.66 g $MgCl_2.6H_2O$ and 0.18 g $NaHCO_3$ in 1 L water). All data is collected at time=1 hour.

Table 3 shows the synergy index for various ratios of THPS:glutaraldehyde at time=1 hour for various bacteria.

TABLE 3

| | Synergy Index | | | |
| --- | --- | --- | --- | --- |
| | Aerobic bacteria | | | Anaerobic bacteria |
| Active weight ratio of THPS to Glut | Standard bacteria | Oil/gas field aerobic bacteria | Standard marine bacterium | Oil/gas field SRB bacteria |
| 10:1 | NA | NA | NA | 1.05 |
| 8:1 | 1:00 | 1.00 | 1.00 | 1.06 |
| 6:1 | 1.00 | 1.00 | 1.00 | 0.71 |
| 4:1 | 0.67 | 0.67 | 0.67 | 0.73 |
| 2:1 | 1.00 | 1.00 | 1.00 | 0.78 |
| 1:1 | 1.00 | 1.00 | 1.00 | 1.25 |

Table 4 shows the concentrations needed to achieve at least 3 log bacterial reduction in 1 hour for aerobic bacteria (treatment at a 4:1 ratio of THPS to glutaraldehyde) and for anaerobic sulfate reducing bacteria (treatment at a 6:1 ratio of THPS to glutaraldehyde).

TABLE 4

| | Concentration required to achieve at lease 3 log bacterial reduction in 1 hr (ppm, active) | | | |
| --- | --- | --- | --- | --- |
| | Aerobic bacteria | | | Anaerobic |
| Biocides | ATCC bacterial strains | Oil/ gas field aerobic bacteria | Standard marine bacterium | bacteria Oil/gas field SRB bacteria |
| THPS alone | | 44.49 | | 44.49 |
| THPS/Glut Blend THPS | | 23.74 | | 25.43 |
| Blend Glutaraldehyde | | 5.93 | | 4.24 |
| Glutaraldehyde alone | | 44.49 | | 29.67 |

It will be apparent to those skilled in the art that various modifications and variations can be made to the present invention without departing from the scope of the invention. Thus, it is intended that the present invention cover the modifications and variations of this invention provided they come within the scope of the appended claims and their equivalents.

What is claimed is:

1. A formulation for reducing or inhibiting increase in the concentration of anaerobic microbes in a water-based fluid or a system used with a water-based fluid, the formulation comprising glutaraldehyde and a hydroxymethyl-substituted phosphorus compound selected from the group consisting of tetrakis(hydroxymethyl)phosphonium salts, $C_1$-$C_3$ alkyl- and alkenyltris(hydroxymethyl)phosphonium salts and tris(hydroxymethyl)phosphine;

wherein the ratio of hydroxymethyl-substituted phosphorus compound to glutaraldehyde is in the range of about 2:1 to about 6:1.

2. The formulation of claim 1, further comprising water.

3. The formulation of claim 1, wherein the hydroxymethyl-substituted phosphorus compound is tetrakis(hydroxymethyl)phosphonium sulfate.

4. The formulation of claim 1, wherein the formulation is substantially free of quaternary ammonium compounds.

5. The formulation of claim 1, wherein the formulation includes at least one anionic polymer, demulsifier, corrosion inhibitor, scale inhibitor and/or surfactant.

6. A method of reducing or inhibiting increase in the concentration of anaerobic microbes in a water-based fluid, the method comprising:

contacting the water-based fluid with the composition of claim 1.

7. The method of claim 6, wherein the hydroxymethyl-substituted phosphorus compound is tetrakis)hydroxymethyl)phosphonium sulfate.

8. The method of claim 6, wherein the water-based fluid is oilfield or gas field water or fluid, hydrocarbon oil and gas, pulp or paper water or slurry, cooling water, boiler water, industrial process water, ballast water, wastewater, a metalworking fluid, water-based slurry, an ink or tape-joint compound, a water-based household product or personal care product, latex, paint, a coating, or a system used therewith.

9. The method of claim 6, wherein the combined concentration of glutaraldehyde and hydroxymethyl-substituted phosphorus compound in the water-based fluid is in the range of about 5 ppm to about 1500 ppm.

10. The method of claim 6, wherein the combined concentration of glutaraldehyde and hydroxymethyl-substituted phosphorus compound in the water-based fluid is in the range of about 10 ppm to about 500 ppm.

11. The method of claim 6, wherein during the contacting step, the water-based fluid is substantially free of quaternary ammonium compounds.

12. The method of claim 6, wherein during the contacting step, the water-based fluid includes at least one anionic polymer, demulsifier, corrosion inhibitor, scale inhibitor and/or surfactant.

13. The method of claim 6, wherein the glutaraldehyde and hydroxymethyl-substituted phosphorus compound are added to the water-based fluid at substantially the same time.

14. A method of reducing or inhibiting increase in the concentration of anaerobic microbes in a water-based fluid in an anaerobic environment or in an anaerobic part of a system used with a water-based fluid, the method comprising:
   contacting the water-based fluid with the composition of claim 1.

* * * * *